(12) United States Patent
Sim et al.

(10) Patent No.: US 8,871,950 B1
(45) Date of Patent: Oct. 28, 2014

(54) PROCESS FOR PREPARING (+)-POLYOXAMIC ACID

(71) Applicant: Korea Institute of Science and Technology, Seoul (KR)

(72) Inventors: Tae Bo Sim, Daegu (KR); Ho Jong Yoon, Seoul (KR); Eun Joo Roh, Seoul (KR)

(73) Assignee: Korea Institute of Science and Technology (KIST), Seoul (KR)

( * ) Notice: Subject to any disclaimer, the term of this patent is extended or adjusted under 35 U.S.C. 154(b) by 0 days.

(21) Appl. No.: 14/065,793

(22) Filed: Oct. 29, 2013

(51) Int. Cl.
C07D 203/10 (2006.01)
C07C 229/08 (2006.01)
C07C 227/02 (2006.01)

(52) U.S. Cl.
CPC .................................. *C07C 227/02* (2013.01)
USPC .......................................... 548/968; 562/553

(58) Field of Classification Search
None
See application file for complete search history.

(56) References Cited

FOREIGN PATENT DOCUMENTS

KR          2011087977 A    *   8/2011

OTHER PUBLICATIONS

"Asymmetric Dihydroxylation of Aziridine-Enoate : Expedient Synthetic Route for Polyhydroxylated Amine Natural Product", The $110^{th}$ General Meeting of the Korean Chemical Society, Oct. 17-19, 2012, pp. 1-1.
H. Kuzuhara, H. Oruhi, S.Emoto. Agr. Biol. Chem,. 1973, 37, 949-951.
A. Tarrade, R. H. Dodd. J. Org. Chem. 2003, 68, 9521-9524.
Y. Lee, H.G. Park. J. Org. Chem. 2011, 76, 740-743.

* cited by examiner

*Primary Examiner* — Michael Barker
(74) *Attorney, Agent, or Firm* — Staas & Halsey LLP

(57) ABSTRACT

The present invention relates to a method for preparing (+)-polyoxamic acid and a novel intermediate compound synthesized during preparation thereof.
The preparation method according to the present invention allows preparation of (+)-polyoxamic acid with high optical purity in high yield. In particular, the preparation method is useful for mass production because the process is simple.

7 Claims, No Drawings

PROCESS FOR PREPARING (+)-POLYOXAMIC ACID

CROSS-REFERENCE TO RELATED APPLICATIONS

This application claims priority under 35 U.S.C. §119 to Korean Patent Application No. 10-2012-0131916, filed on Nov. 20, 2012, in the Korean Intellectual Property Office, the disclosure of which is incorporated herein by reference in its entirety.

BACKGROUND (a) Technical Field

The present invention relates to a novel process for preparing (+)-polyoxamic acid.

(b) Background Art (+)-Polyoxamic acid, represented by Chemical Formula 1, is an amino acid that is comprised of five carbons that are all functionalized and possesses three contiguous stereogenic centers. Its chemical name is (2S,3S,4S)-2-amino-3,4,5-trihydroxypentanoic acid.

[Chemical Formula 1]

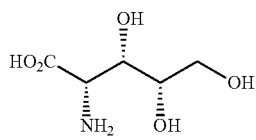

(+)-Polyoxamic acid is the key component of Polyoxins, natural peptidyl nucleoside antibiotics. Polyoxins were first isolated from *Streptomyces cacoi* var. *aseonsis*, and members of this family possess potent biological activities against the chitin synthetase of *Candida albicans*, a human fungal pathogen. So, they have been utilized as agricultural fungicides.

The first total synthesis of (+)-polyoxamic acid was reported in 1973 (H. Kuzuhara, H. Oruhi, S. Emoto. *Agr. Biol. Che.* 1973, 37, 949-951), and lots of methods for synthesizing this compound have been reported. A number of routes for the synthesis of this substance have been described, nearly all of which use chiral substances (e.g., carbohydrates) as starting materials (A. Tarrade, R. H. Dodd. *J. Org. Chem.* 2003, 68, 9521-9524). One exception to this general trend is found in the route for preparation of (+)-polyoxamic acid that utilizes an enantioselective phase-transfer conjugate addition reaction followed by an asymmetric dihydroxylation process (Y. Lee, H. G. Park. *J. Org. Chem.* 2011, 76, 740-743). So, almost all the synthetic routes that have been reported have limitation for preparation of the target compound in large quantity and with proper chirality.

The inventors of the present invention have developed an efficient and stereoselective route for the synthesis of (+)-polyoxamic acid, which begins with a commercially available chiral aziridine that until now has not been utilized as a starting material for the preparation of this target.

SUMMARY

The present invention is directed to providing a novel process for preparing (+)-polyoxamic acid. The present invention is also directed to providing novel intermediate compounds synthesized during preparation of (+)-polyoxamic acid.

In an aspect, the present invention provides a method for preparing (+)-polyoxamic acid, including:

a) preparing a compound represented by Chemical Formula 6 by regioselective aziridine ring opening followed by hydrolysis;

b) preparing a carboxylic acid compound represented by Chemical Formula 7 by Jones oxidation of the compound represented by Chemical Formula 6; and c) preparing a compound represented by Chemical Formula 1 by deprotecting the carboxylic acid compound represented by Chemical Formula 7.

[Scheme 1]

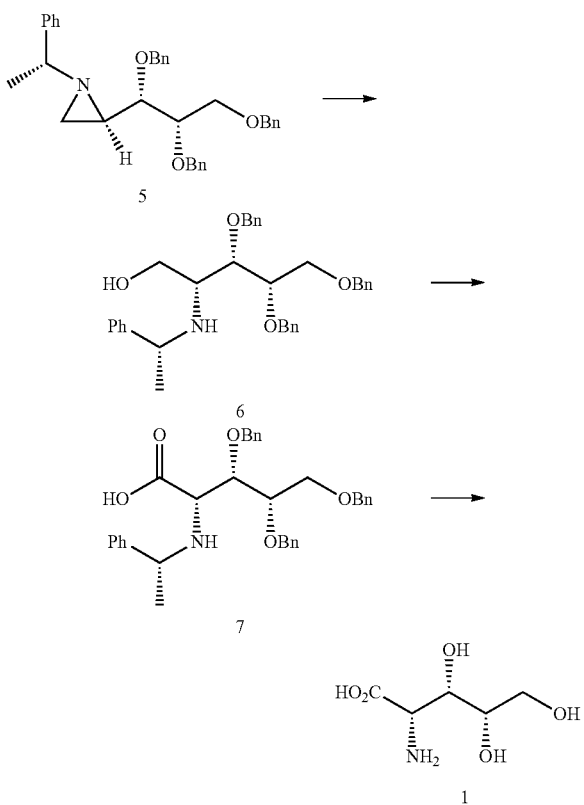

In Scheme 1, Bn represents 'benzyl'.

In another aspect, the present invention provides a synthetic intermediate compound for synthesis of (+)-polyoxamic acid selected from:

(2R,3S)-ethyl 2,3-dihydroxy-3-((R)-1-((R)-1-phenylethyl)aziridin-2-yl)propanoate (compound 4);

(R)-1-((R)-1-phenylethyl)-2-((1S,2S)-1,2,3-tris(benzyloxy)propyl)aziridine (compound 5);

(2R,3S,4S)-3,4,5-tris(benzyloxy)-2-(((R)-1-phenylethyl)amino)pentan-1-ol (compound 6); and (2S,3S,4S)-3,4,5-tris(benzyloxy)-2-(((R)-1-phenylethyl)amino)pentanoic acid (compound 7).

Other features and aspects of the present invention will be apparent from the following detailed description, drawings and claims.

DETAILED DESCRIPTION

Hereinafter, reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

As described in Scheme 1, optically pure (+)-polyoxamic acid is prepared from commercially available 1-(R)-α-methylbenzylaziridine-2-methanol represented by Chemical Formula 2 as starting material.

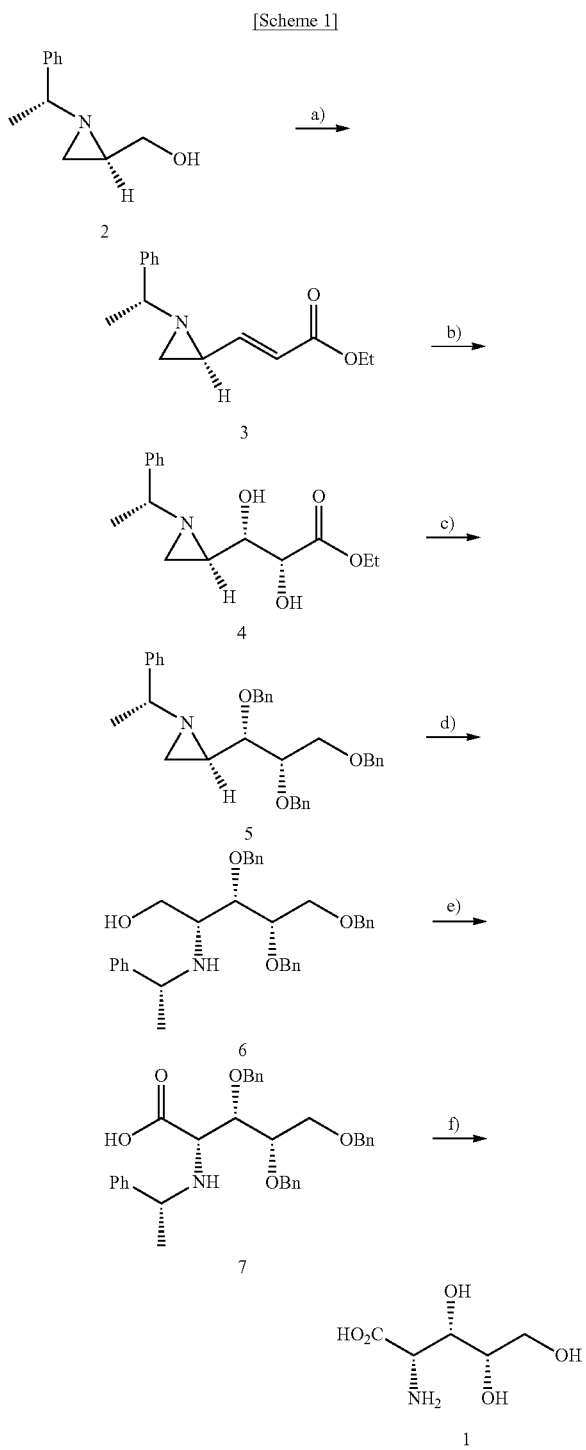

The synthetic process described in scheme 1 is specifically described below. In process a), after oxidation of aziridinylmethanol represented by Chemical Formula 2 by the Swern method, the crude reaction mixture is subsequently reacted with ethyl diethyl phosphonoacetate in the presence of a base to synthesize the ester compound represented by Chemical Formula 3.

Swern oxidation is the reaction for oxidation of primary alcohol to aldehyde and in the present invention it is proceeded in dichloromethane solvent at −90 to −50° C. Horner-Wadsworth-Emmons olefination of the resulting aldehyde using triethyl phosphonoacetate in the presence of an amine base in tetrahydrofuran solvent at room temperature generates the compound represented by Chemical Formula 3 incorporated with ester and olefin.

In process b), the compound represented by Chemical Formula 3 is diastereoselectively dihydroxylated for the synthesis of the compound represented by Chemical Formula 4. The diastereoselective dihydroxylation is proceeded with AD-mix alpha and methanesulfonamide in t-butanol/water solvent at −20 to 20° C.

In process c), the ester functional group of the compound represented by Chemical Formula 4 is reduced to hydroxyl group, and the remaining three free hydroxy functional groups are protected with benzyl protecting groups, for the synthesis of the compound represented by Chemical Formula 5. The reduction is proceeded using an ordinary reducing agent (e.g. $NaBH_4$). After the reduction is ended, a benzyl protecting group can be introduced without further purification. The benzyl protection is proceeded in DMF solvent in the presence of a base. Here, the base can be selected from a hydride with an alkali metal, a hydroxide with an alkali metal, a carbonate salt, a hydrogen carbonate salt, a sulfate salt, a hydrogen sulfate salt, etc. (e.g. NaH, NaOH, KOH, $Na_2CO_3$, $NaHCO_3$, $Na_2SO_4$, $NaHSO_4$). The base can be used in an amount of about 3 equivalents, specifically 1-1.5 equivalents.

In process d), the compound represented by Chemical Formula 5 is subjected to regioselective aziridine ring opening reaction followed by hydrolysis to prepare the compound represented by Chemical Formula 6. The ring opening reaction is proceeded using excess amount of acetic acid in dichloromethane solvent at room temperature. When the opening reaction is finished, hydrolysis of the crude reaction mixture can be proceeded without further purification. The hydrolysis reaction is proceeded by using inorganic bases, which are already described in process c).

In process e), the compound represented by Chemical Formula 6 is subjected to Jones oxidation to synthesize the carboxylic acid compound represented by Chemical Formula 7. The Jones oxidation is proceeded using a Jones reagent in acetone at −20 to 20° C.

In process f), the carboxylic acid compound represented by Chemical Formula 7 is deprotected to synthesize the target compound (+)-polyoxamic acid represented by Chemical Formula 1. In this deprotection process, all the protecting groups in the compound represented by Chemical Formula 7 are removed. Specifically, this deprotection reaction is proceeded using a palladium compound and an acid catalyst in hydrogen atmosphere (hydrogenolysis). The acid catalyst may be HCl, $H_2SO_4$, etc., and the palladium compound may be $Pd(OH)_2$, $PdCl_2$, etc.

According to the preparation method of the present invention, highly optically pure (+)-polyoxamic acid represented by Chemical Formula 1 can be prepared with high yield.

The present invention also provides synthetic intermediate compounds prepared during the preparation of (+)-polyoxamic acid according to Scheme 1. That is to say, all the intermediate compounds represented by Chemical Formulas 4, 5, 6 and 7 are novel compounds and also are important intermediate chemicals for the synthesis of (+)-polyoxamic acid.

EXAMPLES

The present invention will be described in more detail through examples. The following examples are for illustrative purposes only and it will be apparent to those skilled in the art not that the scope of this invention is not limited by the examples.

Example 1

(2S,3S)-Methyl 2,3-dihydroxy-3-((R)-1-((R)-1-phenylethyl)aziridin-2-yl)propanoate

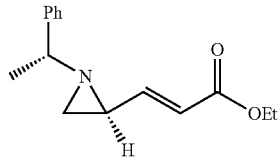 [SMILES: CCOC(=O)/C=C/[C@H]1CN1[C@H](C)c1ccccc1]

To a solution of (COCl)$_2$ (4.1 mL, 47.73 mmol, 1.2 equiv) in CH$_2$Cl$_2$ (100 mL, 0.3 M) was slowly added DMSO (7 mL, 99.43 mmol, 2.5 equiv) at −78° C. After 30 min, a solution of 5 (7.05 g, 39.77 mmol) in CH$_2$Cl$_2$ (80 mL, 0.5 M) was added. After 30 min, Et$_3$N (22 mL, 119.3 mmol, 4 equiv) was added at −78° C. and the reaction mixture was stirred for 30 min at 0° C. The mixture was quenched with water and then extracted with CH$_2$Cl$_2$. The combined organic layer was dried over anhydrous MgSO$_4$, filtered and concentrated in vacuo. The resulting aldehyde was used without further purification. To a solution of the aldehyde in THF (80 mL) was added triethyl phosphonoacetate (9.5 mL, 47.7 mmol, 1.2 equiv) at room temperature. After 10 min at room temperature, LHMDS (47.7 mL, 47.7 mmol, 1.2 equiv, 1 M in THF) was added. The reaction mixture was stirred for 1 hr at room temperature and then quenched with water. The mixture was extracted with ethyl acetate. The combined organic layer was dried over anhydrous MgSO$_4$, filtered and concentrated in vacuo. The resulting crude product was purified by silica gel flash column chromatography with ethyl acetate/hexane (1/6) to afford the title product. Yield: 7.02 g (28.63 mmol, 72% over 2 steps); yellow oil.

$^1$H NMR (400 MHz, CDCl$_3$): δ=7.40-7.31 (m, 4H), 7.28-7.23 (m, 1H), 6.76 (dd, J=8.0 Hz, 15.6 Hz, 1H), 6.14 (d, J=15.6 Hz, 1H), 4.21 (q, J=6.8 Hz, J=14.0 Hz, 2H), 2.56 (q, J=6.4 Hz, J=13.2 Hz, 1H), 2.16-2.11 (m, 1H), 1.80 (d, J=3.2 Hz, 1H), 1.66 (d, J=6.4 Hz, 1H), 1.42 (d, J=6.8 Hz, 3H) 1.29 (t, J=7.1 Hz, 3H).

Example 2

(2R,3S)-Ethyl 2,3-dihydroxy-3-((R)-1-((R)-1-phenylethyl)aziridin-2-yl)propanoate

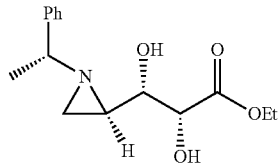 [SMILES: CCOC(=O)[C@H](O)[C@@H](O)[C@H]1CN1[C@H](C)c1ccccc1]

To a solution of (2S,3S)-methyl 2,3-dihydroxy-3-((R)-1-((R)-1-phenylethyl)aziridin-2-yl)propanoate (3.3 g, 13.3 mmol) in t-BuOH/H$_2$O (60 mL, 0.2 M/60 mL, 0.2 M) were added AD-mix α (33 g, 1000 w/w %) and methanesulfonamide (1.9 g, 19.9 mmol, 1.5 equiv) at 0° C. The reaction mixture was stirred for 24 hrs and quenched with water. The aqueous layer was extracted with ethyl acetate and the combined organic layer was washed with brine, dried over MgSO$_4$, filtered through a pad of celite, and concentrated under reduced pressure. The residue was subjected to silica gel column chromatography with ethyl acetate/hexane (2/3) to afford the title product (diastereomeric mixture, ratio=7/1). Yield: 2.3 g (62%); yellow oil.

$^1$H NMR (400 MHz, CDCl$_3$): δ=7.36-7.29 (m, 4H), 7.28-7.23 (m, 1H), 4.31-4.26 (q, J=6.8 Hz, J=14.0 Hz, 2H), 4.25 (bs, 1H), 3.75 (bs, 1H), 2.65-2.60 (q, J=6.4 Hz, J=13.2 Hz, 1H), 2.03 (m, 1H), 1.72 (d, J=3.6 Hz, 1H), 1.48 (d, J=6.8 Hz, 3H), 1.41 (d, J=6.8 Hz, 3H), 1.31 (t, J=7.2 Hz, 3H).

Example 3

(R)-1-((R)-1-Phenylethyl)-2-((1S,2S)-1,2,3-tris(benzyloxy)propyl)aziridine

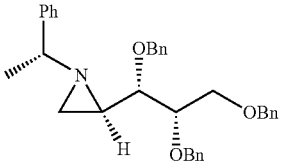 [SMILES: C[C@H](c1ccccc1)N1C[C@@H]1[C@H](OCc1ccccc1)[C@H](COCc1ccccc1)OCc1ccccc1]

To a solution of (2R,3S)-ethyl 2,3-dihydroxy-3-((R)-1-((R)-1-phenylethyl)aziridin-2-yl)propanoate (1 g, 3.57 mmol) in EtOH was added LiCl (756 mg, 17.85 mmol, 5 equiv) and NaBH$_4$ (680 mg, 17.85 mmol, 5 equiv) at 0° C. The reaction mixture was stirred for 20 hrs at 0° C. and quenched with water. The reaction mixture was partitioned between ethyl acetate and water. The aqueous layer was extracted with ethyl acetate and the combined organic layers were dried over MgSO$_4$, filtered through a pad of celite and concentrated in vacuo. The resulting alcohol was used without further purification. To a slurry of NaH (471 mg, 11.78 mmol, 60% dispersion in mineral oil, 3.3 equiv) in DMF (6 mL, 2 M) was added a solution of the resulting alcohol in DMF (7 mL, 0.5 M) at 0° C. After 30 min, BnBr (1.4 mL, 11.78 mmol, 3.3 equiv) was added. The reaction mixture was stirred for 6 hrs at room temperature, diluted with ethyl acetate and quenched with water. The mixture was extracted with ethyl acetate. The combined organic layer was washed with brine, dried over anhydrous MgSO$_4$, filtered and concentrated under reduced pressure. The resulting crude product was purified by silica gel flash chromatography with ethyl acetate/hexane (1/9 to 1/6) to afford the title product. Yield: 1.29 g (71% over 2 steps); yellow oil.

$^1$H NMR (400 MHz, CDCl$_3$) δ 7.40-7.24 (m, 20H), 5.02 (d, J=11.6 Hz, 1H), 4.76 (d, J=9.6 Hz, 1H), 4.63 (d, J=12.0 Hz, 1H), 4.28 (s, 2H), 3.67 (m, 3H), 3.21 (dd, J=3.6 Hz, J=8.8 Hz, 1H), 2.46 (q, J=6.4 Hz, J=13.2 Hz, 1H), 1.89 (m, 1H), 1.53 (d, J=6.4 Hz, 3H), 1.44 (d, J=3.6 Hz, 1H), 1.09 (d, J=6.8 Hz, 1H).

Example 4

(2R,3S,4S)-3,4,5-Tris(benzyloxy)-2-(((R)-1-phenyl-ethyl)amino)pentan-1-ol

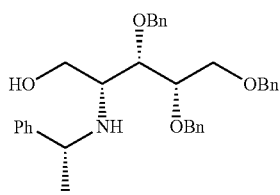 [SMILES: C[C@@H](N[C@H](CO)[C@H](OCc1ccccc1)[C@H](COCc1ccccc1)OCc1ccccc1)c1ccccc1]

To a solution of (R)-1-((R)-1-phenylethyl)-2-((1S,2S)-1,2,3-tris(benzyloxy)propyl)aziridine (340 mg, 0.67 mmol) in CH$_2$Cl$_2$ (2 mL, 0.3 M) was added AcOH (0.38 mL, 6.7 mmol, 10 equiv). The reaction mixture was stirred for 18 hrs at room temperature, diluted with CH$_2$Cl$_2$ and quenched with saturated NaHCO$_3$ solution. The aqueous layer was extracted with CH$_2$Cl$_2$ and the combined organic layer was washed with brine, dried over MgSO$_4$, filtered through a pad of celite and concentrated in vacuo. The resulting acetate was used without further purification. To a solution of the acetate in EtOH (2 mL, 0.3 M) was added KOH (113 mg, 2.1 mmol, 3 equiv). The reaction mixture was stirred for 2 hrs at room temperature, diluted with CH$_2$Cl$_2$ and quenched with water. The aqueous layer was extracted with CH$_2$Cl$_2$ and the combined organic layer was washed with brine, dried over MgSO$_4$, filtered through a pad of celite and concentrated in vacuo. The resulting crude product was purified by silica gel flash chromatography with ethyl acetate/hexane (1/4 to 1/2) to afford the title product. Yield: 225 mg (64% yield over 2 steps); yellow oil.

$^1$H NMR (400 MHz, CDCl$_3$) δ 7.41-7.24 (m, 20H), 4.83 (d, J=11.6 Hz 1H), 4.75 (d, J=11.6 Hz, 1H), 4.68 (d, J=12.0 Hz, 1H), 4.56 (m, 3H), 3.99 (m, 1H), 3.85 (m, 1H), 3.77 (m, 3H), 3.34 (m, 2H), 2.86 (m, 1H), 2.22 (bs, 1H), 1.24 (d, J=6.4 Hz, 3H).

Example 5

(2S,3S,4S)-3,4,5-Tris(benzyloxy)-2-(((R)-1-phenyl-ethyl)amino)pentanoic acid

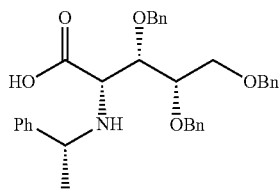 [SMILES: C[C@@H](N[C@H](C(=O)O)[C@H](OCc1ccccc1)[C@H](COCc1ccccc1)OCc1ccccc1)c1ccccc1]

To a solution of (2R,3S,4S)-3,4,5-tris(benzyloxy)-2-(((R)-1-phenylethyl)amino)pentan-1-ol (110 mg, 0.209 mmol) in acetone (2 mL, 0.1 M) was added Jones reagent (0.21 mL, 0.522 mmol, 2.5 M solution in H$_2$O) at 0° C. The reaction mixture was stirred for 4 hrs at 0° C., quenched with isopropyl alcohol and filtered through a pad of celite and washed with CH$_2$Cl$_2$. The reaction mixture was partitioned between CH$_2$Cl$_2$ and water. The aqueous layer was extracted with CH$_2$Cl$_2$ and the combined organic layer was washed with brine, dried over MgSO$_4$, filtered through a pad of celite, and concentrated under reduced pressure. The residue was subjected to silica gel column chromatography with ethyl acetate/hexane (1/2) to CH$_2$Cl$_2$/MeOH (20/1) to afford the title product. Yield: 59 mg (0.11 mmol, 52%); white solid.

$^1$H NMR (400 MHz, CDCl$_3$) δ 7.40-7.02 (m, 20H), 4.75 (m, 2H), 4.64 (m, 1H), 4.54-4.46 (m, 4H), 4.14 (m, 1H), 3.96 (m, 1H), 3.71 (m, 2H), 3.63 (m, 1H), 1.26 (d, J=6.8 Hz, 3H).

Example 6

(+)-Polyoxamic Acid

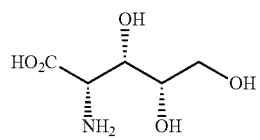

To a solution of (2S,3S,4S)-3,4,5-tris(benzyloxy)-2-(((R)-1-phenylethyl)amino)pentanoic acid (59 mg, 0.109 mmol) in MeOH was added Pd(OH)$_2$ (59 mg). The reaction mixture was flushed with the hydrogen and stirred for 6 hrs under hydrogen atmosphere (50 psi) at room temperature. The reaction mixture was then filtered through a pad of celite and concentrated in vacuo. The resulting crude solid was recrystallized from EtOH/isopropyl alcohol to afford (+)-polyoxamic acid. Yield: 14 mg (78%); white solid.

$^1$H NMR (300 MHz, D$_2$O) δ 4.21 (dd, J=3.3, 2.7 Hz, 1H), 3.93-3.87 (m, 2H), 3.72-3.60 (m, 2H).

As described, highly optically pure (+)-polyoxamic acid could be synthesized easily with high yield according to the preparation method of the present invention.

Accordingly, the present invention is proper for the mass production of Polyoxins, which are agricultural fungicides.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. A method for preparing (+)-polyoxamic acid, Chemical Formula 1, comprising:
preparing a compound represented by Chemical Formula 6 by regioselective aziridine ring opening followed by hydrolysis;
preparing a carboxylic acid compound represented by Chemical Formula 7 by Jones oxidation of the compound represented by Chemical Formula 6; and
preparing a compound represented by Chemical Formula 1 by deprotecting the carboxylic acid compound represented by Chemical Formula 7:

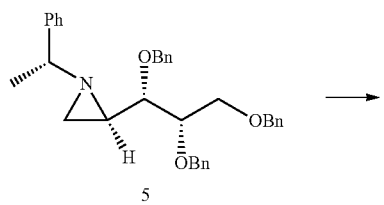

5

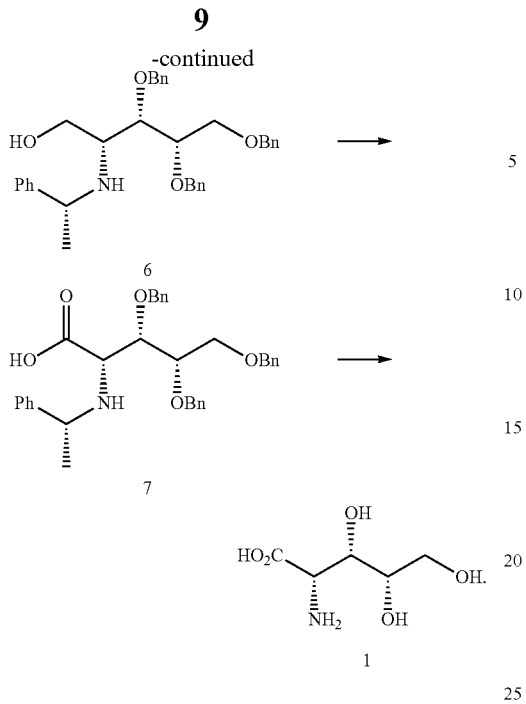

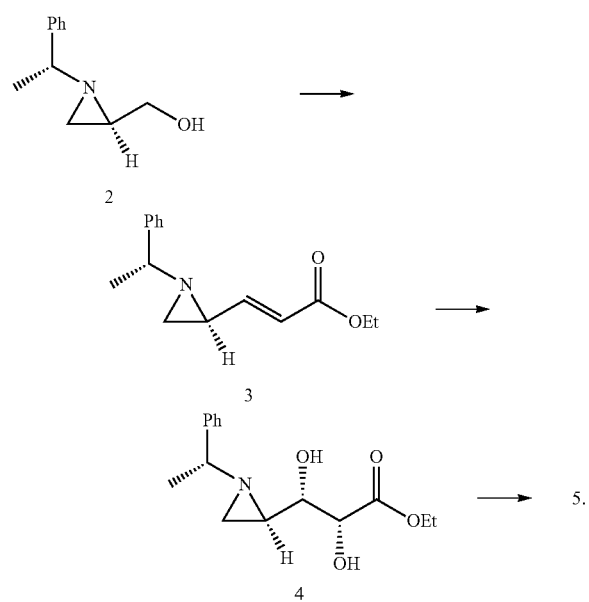

2. The method for preparing (+)-polyoxamic acid according to claim 1, wherein the aziridine ring opening is performed at 20-35° C. using acetic acid.

3. The method for preparing (+)-polyoxamic acid according to claim 1, wherein the Jones oxidation is performed at −20 to 20° C. using a Jones reagent in an acetone solvent.

4. The method for preparing (+)-polyoxamic acid according to claim 1, wherein the deprotection is performed by hydrogenolysis using an acid catalyst and a palladium compound in hydrogen atmosphere.

5. The method for preparing (+)-polyoxamic acid according to claim 1, wherein the deprotection is performed using an acid catalyst selected from HCl and $H_2SO_4$ and a palladium selected from $Pd(OH)_2$ and $PdCl_2$ in hydrogen atmosphere.

6. The method for preparing (+)-polyoxamic acid according to claim 1, wherein the compound represented by Chemical Formula 5 is prepared by:
   preparing an ester compound represented by Chemical Formula 3 by Swern oxidation of an aziridinylmethanol compound represented by Chemical Formula 2 followed by reaction with ethyl diethyl phosphonoacetate in the presence of a base;
   preparing a dihydroxyl-introduced ester compound represented by Chemical Formula 4 by stereoselective dihydroxylation of the compound represented by Chemical Formula 3 using AD-mix-alpha and methanesulfonamide; and
   preparing a compound represented by Chemical Formula 5 having three hydroxyl groups protected with benzyl groups by reduction of the ester of the compound represented by Chemical Formula 4 followed by with benzyl halide in the presence of a base:

7. A synthetic intermediate compound for synthesis of (+)-polyoxamic acid selected from:
   (2R,3S)-ethyl 2,3-dihydroxy-3-((R)-1-((R)-1-phenylethyl)aziridin-2-yl)propanoate (compound 4);
   (R)-1-((R)-1-phenylethyl)-2-((1S,2S)-1,2,3-tris(benzyloxy)propyl)aziridine (compound 5);
   (2R,3S,4S)-3,4,5-tris(benzyloxy)-2-(((R)-1-phenylethyl)amino)pentan-1-ol (compound 6); and
   (2S,3S,4S)-3,4,5-tris(benzyloxy)-2-(((R)-1-phenylethyl)amino)pentanoic acid (compound 7).

* * * * *